United States Patent
Chang et al.

(10) Patent No.: US 11,179,309 B2
(45) Date of Patent: Nov. 23, 2021

(54) HAIR CARE COMPOSITION

(71) Applicant: Conopco, Inc., Englewood Cliffs, NJ (US)

(72) Inventors: Shaokun Chang, Shanghai (CN); Jingjing Liu, Shanghai (CN); Yingying Pi, Shanghai (CN); Raghupathi Subramanian, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 18 days.

(21) Appl. No.: 15/781,341

(22) PCT Filed: Nov. 28, 2016

(86) PCT No.: PCT/EP2016/078982
§ 371 (c)(1),
(2) Date: Jun. 4, 2018

(87) PCT Pub. No.: WO2017/097620
PCT Pub. Date: Jun. 15, 2017

(65) Prior Publication Data
US 2018/0360716 A1 Dec. 20, 2018

(30) Foreign Application Priority Data
Dec. 9, 2015 (WO) ............... PCT/CN2015/096858
Feb. 24, 2016 (EP) .................................... 16157052

(51) Int. Cl.
*A61K 8/49* (2006.01)
*A61K 8/27* (2006.01)
*A61K 8/73* (2006.01)
*A61Q 5/00* (2006.01)

(52) U.S. Cl.
CPC ............ *A61K 8/4933* (2013.01); *A61K 8/27* (2013.01); *A61K 8/737* (2013.01); *A61Q 5/006* (2013.01)

(58) Field of Classification Search
None
See application file for complete search history.

(56) References Cited

U.S. PATENT DOCUMENTS

| | | | |
|---|---|---|---|
| 2008/0206355 A1* | 8/2008 | Schwartz | A61K 8/27 424/604 |
| 2009/0169644 A1* | 7/2009 | Goddinger | A61K 8/922 424/642 |
| 2010/0247472 A1* | 9/2010 | Sau | A61K 8/731 424/70.12 |
| 2012/0071456 A1* | 3/2012 | Chang | A61P 17/00 514/186 |
| 2014/0154200 A1* | 6/2014 | Lizarraga | A61Q 5/006 424/70.12 |
| 2014/0335040 A1* | 11/2014 | Yu | A61K 8/4933 424/70.28 |

FOREIGN PATENT DOCUMENTS

| | | |
|---|---|---|
| WO | WO2006110385 | 10/2006 |
| WO | WO 2010/040671 A2 * | 4/2010 |
| WO | WO2010127924 | 11/2010 |
| WO | WO2016172409 | 10/2016 |

OTHER PUBLICATIONS

Rhodia product description (Sep. 2009).*
English translation of WO 2010/040671A2 (Apr. 2010).*
Michael Fevola (Johnson & Johnson, Mar. 25, 2013).*

* cited by examiner

*Primary Examiner* — Bethany P Barham
*Assistant Examiner* — Barbara S Frazier
(74) *Attorney, Agent, or Firm* — Foley & Lardner LLP

(57) ABSTRACT

This invention relates to a hair care composition which provides the desired anti-dandruff efficacy with uniform deposition of the active materials on hair/scalp. This is achieved through a judicious combination of a specific cationic deposition polymer and selective anti-dandruff agent of the right particle size.

11 Claims, No Drawings

HAIR CARE COMPOSITION

FIELD OF THE INVENTION

This invention relates to a hair care composition which provides desired anti-dandruff efficacy with optimum deposition of the active materials on hair/scalp to ensure maximum anti-microbial efficacy. This is achieved by ensuring maximisation of the active deposition while ensuring uniformity of deposition. In particular, the present invention relates to a hair care composition comprising a judicious combination of a specific cationic deposition polymer and selective anti-dandruff agent of the right particle size.

BACKGROUND OF THE INVENTION

Hair care compositions generally provide cleansing or conditioning benefits or a combination of the two. Such compositions typically comprise one or more cleansing surfactants which generally aid in cleaning the hair and the scalp free of undesirable soil, particles and fatty matter. Conditioning benefit is achieved by including one or more conditioning agents in the hair care composition. Conditioning benefit is delivered with an oily material being deposited onto the hair resulting in the formation of a film, which makes the hair easier to comb when wet and more manageable when dry.

Additionally, anti-dandruff benefit has been provided through hair care compositions. Dandruff is an issue that affects many people globally. The condition is manifested by the shedding of clumps of dead skin cells from the scalp. These are white in colour and provide an aesthetically displeasing appearance. A factor that contributes to dandruff are certain members of the *Malassezia* yeasts. To combat these, anti-dandruff products have included certain zinc salts which have anti-fungal activity, for example zinc pyrithione (ZPTO). Such a product has to perform as a hair cleansing shampoo, while mitigating the causes of dandruff. An example of a known anti-dandruff shampoo comprises sodium lauryl ether sulfate (an ethoxylated anionic surfactant) in combination with an anti-dandruff agent. Typical anti-dandruff agents used in hair care are metal pyrithione e.g zinc pyrithione (ZPTO), octopirox (piroctone olamine), azole antimicrobials (e.g. climbazole), selenium sulfide and combinations thereof. Of these, zinc pyrithione is a particulate material.

Cationic polymers are often used to enhance the deposition of the conditioning agent and/or particulate material like zinc pyrithione onto the hair. These polymers may be synthetic or natural polymers that have been modified with cationic substituents.

A problem associated with solving the problem of dandruff through such shampoos is that one needs to optimise a large number of parameters, most of which are still being researched, in order to achieve the end benefit of reducing or eliminating dandruff. The present inventors through extensive experimentation have deduced that the type of cationic deposition polymer in terms of molecular weight and cationic degree of substitution and the particle size of the ZPTO are critical, in order to maximise the deposition of ZPTO while ensuring the desired uniformity in deposition to enhance anti-dandruff efficacy. They not only observed the above mentioned benefits but at the optimum conditions the enhanced anti-microbial efficacy has also been demonstrated. Further, these parameters also have an implication on the feel and appearance of the hair after use of the hair care product.

In summary, the present inventors have found that the above contrasting requirements can be met by using a combination of a cationic polymer of specific molecular weight and cationic charge density with a zinc based anti dandruff particle active of a specific particle size in a hair care composition.

DE102008050430 (2009, Henkel) discloses an antidandruff composition containing, based on its total weight: A) 0.5 to 20 wt % of at least one anionic sulfate and/or sulfonate surfactant, B) from 0.05 to 5 wt % of zinc pyrithione having a particle size less than 2 microns and C) from 0.05 to 5 wt % of a cationic polygalactomannan or derivative of the cationic polygalactomannan with a cationic charge density of 0.1 to 1.5 meq/g and a molecular weight of 500,000 to 3,000,000.

The present inventors have found that the above specification of ZPTO particle size and the cationic polygalactomannan specification is too broad and not all of the ranges within it will provide the desired flocculation profile necessary to get the benefits of the present invention.

SUMMARY OF THE INVENTION

According to the first aspect of the present invention there is provided a hair care composition comprising from
(i) 0.01 to 3.0% by weight of a zinc-based antidandruff agent having a average particle size of 0.25 to 8 micrometer; and
(ii) 0.04 to 2.0% by weight of a cationic modified guar deposition polymer having a molecular weight of from 1.0 million to 1.5 million Dalton and a cationic degree of substitution of from 0.16 to 0.20.

According to the second aspect of the present invention there is provided a method of maximizing the deposition of a zinc-based antidandruff agent on to scalp with a uniform deposition profile comprising the steps of applying a composition as claimed in any one of the preceding claims on to the desired scalp surface followed by rinsing the surface with water.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilized in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated. In other words, in specifying any ranges of values, any particular upper value can be associated with any particular lower value.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

By "a Hair Care Composition" as used herein, is meant to include a composition for topical application to hair and/or scalp of mammals, especially humans. Such a composition may be generally classified as leave-on or rinse off, and includes any product applied to a human body for also improving appearance, cleansing, odor control or general aesthetics. The composition of the present invention can be in the form of a liquid, lotion, cream, foam, scrub, gel, or bar. Non-limiting examples of such compositions include leave-on hair lotions, creams, and wash-off shampoos, conditioners, shower gels, or toilet bar. The composition of the present invention is preferably a wash-off composition, especially preferred being a shampoo or a conditioner and most preferably a shampoo.

Degree of Substitution

"Degree of substitution", as used herein, refers to the average number of moles of cationic groups per mole of sugar unit. The degree of substitution (DS) is measured using $^1$H NMR in a solvent of deuterium oxide (D$_2$O) and deuterium chloride (DCl) mixture. For example, the DS of guar hydroxylpropyltrimonium chloride is measured using $^1$H NMR and the spectrum is recorded at 25° C. The sample for measurement using NMR is prepared as follows. The polymer sample is dispersed in D$_2$O and DCl solution with stirring, and then put into a boiling water bath for one hour. After cooling to the room temperature, the sample is filtered and the clear filtrate is poured into an NMR tube.

The peak corresponding to the nine methyl protons of the quaternary ammonium group on guar units, which appears between 3.1-3.3 ppm, is integrated as A1. The multiplet of peaks corresponding to the anomeric protons on sugar ring and protons on CH$_2$ and CH groups of the cationic substituent, which appear between 3.3-4.5 ppm, are also integrated as A2. Therefore, the DS for the case of the cationizing agent 2,3-epoxypropyltrimethylammonium chloride may be calculated as follows:

Cationic charge density in milliequivalents per gram (meq/g) =

$$\frac{DS \times 1000}{162 + 151 \times DS}$$

Cationic Charge Density

"Cationic charge density", as used herein, refers to the number of cationic charges per weight unit of a given polymer. Cationic charge density can be calculated from the degree of substitution as described in WO 2013/011122, the disclosure of which is hereby incorporated by reference in its entirety but especially page 8 lines 8-17. For example, for cationically-modified guar polymer obtained by reacting with 2,3-epoxypropyltrimethylammonium chloride, the cationic charge density may be calculated from the DS using the following equation:

$$DS = \frac{(A1/9)}{(A2 - A1 \times 5/9)/6}$$

Water-Insoluble

"Water-insoluble", as used herein, refers to the solubility of a material in water at 25° C. and atmospheric pressure being 0.1% by weight or less.

Molecular Weight

"Molecular weight", as used herein, refers to the weight average molecular mass of a given polymer, The weight average molecular weight (WAVG MW) of cationic guar gum herein is determined by SEC (Size Exclusion chromatography) analysis using an ELSD (Evaporative Light Scattering Detector). The MW is determined against a Pullulans standard calibration set.

Average Particle Size:

The average particle size as used herein refers to the volume average particle size as measured using light scattering technique with a Malvern Mastersizer 2000 instrument. The settings used for the measurement included a particle absorption of 0.1, with water as the dispersant an obscuration limit of 10-12% and a pump-speed of 960 rpm. The average particle size of a sample was measured from the particle size distribution curves as an average of three sample readings.

According to the first aspect of the present invention, there is provided a hair care composition comprising a zinc-based antidandruff agent having a average particle size of 0.25 to 8 micrometer; and a cationic modified guar deposition polymer having a molecular weight of from 1.0 million to 1.5 million Dalton and a cationic degree of substitution of from 0.16 to 0.20.

The hair care composition comprises a zinc based anti-dandruff agent. The zinc based anti-dandruff agent is preferably water insoluble and more preferably zinc pyrithione. Zinc pyrithione (ZPTO) shorthand for zinc 1-hydroxy-2-pyridinethione is most preferred. The zinc based antidandruff agent is present at a level of from 0.01 to 3%, preferably from 0.01 to 1.5%, more preferably from 0.05 to 1.5% based on weight of the composition. It has been found by way of the present invention that the particle size of the zinc based antidandruff agent is important for obtaining the benefits of the present invention. The average particle size (D$_{50}$) of the zinc based antidandruff agent is from 0.25 to 8 micrometer, preferably from 0.5 to 8.0 micrometer, more preferably from 1.0 to 7.5 micrometer, and further more preferably from 1.0 to 5.0 micrometer, and most preferably from 1 to 3 micrometer. ZPTO as per the above particle size is available Kolon Life Science Inc., Sino Lion (USA) Ltd, Lonza and other suppliers.

The composition also comprises cationic modified guar deposition polymer having a molecular weight of from 1.0 million to 1.5 million Dalton and a cationic degree of substitution of from 0.16 to 0.20. Cationic guar deposition polymer is preferably guar hydroxypropyltrimonium chloride. Guar polymer predominantly contains galactomannan polymer chains. This polymer is available at various molecular weights and degree of cationic substitutions depending on how much the guar has been hydrolysed and cationised. It is important as per the present invention that the cationic modified guar deposition polymer has a molecular weight of from 1.0 million to 1.5 million and a degree of substitution (DS) of from 1.6 to 0.20. This DS value corresponds to a charge density of from 0.85 to 1.05.

Generally for cationic polysaccharide polymers, the hydroxyl groups of the non-modified monomeric sugar ring units are the sites for cationic substitution. Degree of substitution (DS) is typically in the range from 0 to 3 due to the fact that the monomeric sugar unit of most polysaccharide has in average three hydroxyl groups available for substitution. In addition to the DS, the cationic charge on polymers can also be quantified as cationic charge density. DS has previously been determined by different methods. For example, the cationic charge density of the polymer has in some cases been calculated based on a percent nitrogen content determined via the Kjeldahl method as described in US Pharmacopoeia under chemical tests for nitrogen determination and is expressed in milliequivalents (meq) per gram. The cationic charge density of the polymer in the present invention is, however, calculated from the degree of substitution, which is measured by $^1$H NMR in a solvent of deuterium oxide ($D_2O$) and deuterium chloride (DCl) mixture.

In many cases the DS obtained from $^1$H NMR measurement may not be suitable to be compared with that obtained from Kjeldahl method, due to the fact that the two methods are influenced by different factors.

In the wide spectrum of molecular weights of guars available, the cationic guar for use in the present invention has a molecule weight which is considered a 'medium' molecular weight. In the wide range of charge densities, the above range for use in the present invention is considered a 'medium' range. The cationic modified guar deposition polymer is preferably present in 0.04 to 0.5%, more preferably 0.08 to 0.25% by weight of the composition.

Without wishing to be bound by theory the inventors believe that the unique combination of the zinc based antidandruff agent with the specific particle size and the cationic guar with specific molecular weight and degree of substitution provides controlled flocculation, which ensures uniform distribution on the various surfaces of the scalp. Further, the specific size of the zinc based anti-dandruff agent is believed to enable better retention on scalp after rinsing thereby leading to higher deposition.

The pH of the composition is preferably equal to or higher than 4.0, more preferably in the range of 5.0 to 7.0.

The composition as per the invention preferably additionally comprises a zinc compound. The presence of additional zinc compound in the composition is believed to improve the antidandruff efficacy of the zinc based antidandruff agent. Suitable zinc compounds are zinc oxide, zinc citrate, zinc malonate, zinc carbonate or combinations thereof. The zinc compound is preferably present in 0.1 to 3%, more preferably 0.1 to 1.5% by weight of the composition.

The composition as per the invention preferably additionally comprises a conazole fungicide. Preferably the conazole fungicide is selected form ketoconazole, climbazole or mixtures thereof. The azole fungicide is preferably included in 0.01 to 2%, more preferably 0.025 to 0.75% by weight of the composition. The presence of a conazole fungicide is believed to improve the deposition of zinc pyrithione.

The composition preferably additionally comprises a vitamin B3 compound. The preferred vitamin B3 compound is niacinamide.

Niacinamide has the structure as given below

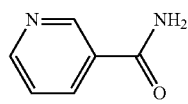

Niacinamide is known for secretion of AMPs from keratinocytes. The AMPs thus secreted provides for improving the immunity of the external surface of the body e.g. on the scalp. Thus with the use of niacinamide in the composition of the invention the anti-dandruff efficacy is expected to be enhanced not just through anti-fungal activity of the zinc based anti-dandruff agent but by providing a boost to the scalp's own protection shield against germs, through use of niacinamide. It is expected that this combination could provide long-lasting protection e.g. up to 24 hours of protection against germs.

Niacinamide is preferably present in 0.1 to 5%, more preferably 0.5 to 5%, further more preferably 0.5 to 3%, and optimally 1.0 to 3.0% by weight of the composition.

As per an especially preferred aspect of the invention, the composition is a shampoo. The composition of the invention especially shampoos are formulated preferably with an anionic surfactant e.g. an alkyl sulphate and/or ethoxylated alkyl sulfate surfactant. These anionic surfactants are preferably present at a level of from 2 to 16%, more preferably from 3 to 16% by weight of the composition. Preferred alkyl sulfates are C8-18 alky sulfates, more preferably C12-18 alkyl sulfates, preferably in the form of a salt with a solubilising cation such as sodium, potassium, ammonium or substituted ammonium. Examples are sodium lauryl sulfate (SLS) or sodium dodecyl sulfate (SDS).

Preferred alkyl ether sulfates are those having the formula: $RO(CH_2CH_2O)_nSO_3M$; wherein R is an alkyl or alkenyl having from 8 to 18 (preferably 12 to 18) carbon atoms; n is a number having an average value of greater than at least 0.5, preferably between 1 and 3, more preferably between 2 and 3; and M is a solubilising cation such as sodium, potassium, ammonium or substituted ammonium. An example is sodium lauryl ether sulfate (SLES).

Preferred ethoxylated alkyl sulfate anionic surfactant is sodium lauryl ether sulfate (SLES) having an average degree of ethoxylation of from 0.5 to 3, preferably 1 to 3. The composition as per the invention optionally and preferably additionally comprises a betaine surfactant. In a preferred embodiment, the composition comprises from 0.1 to 10 wt. %, preferably from 0.5 to 8 wt. %, more preferably from 1 to 5 wt. % of a betaine surfactant, preferably an alkyl amidopropyl betaine, for example cocamidopropyl betaine.

Shampoo compositions according to the invention may comprise one or more further anionic cleansing surfactants which are cosmetically acceptable and suitable for topical application to the hair.

Examples of further suitable anionic cleansing surfactants are the alkaryl sulphonates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphosuccinates, alkyl ether phosphates and alkyl ether carboxylic acids and salts thereof may contain from 1 to 20 ethylene oxide or propylene oxide units per molecule.

Typical anionic cleansing surfactants for use in shampoo compositions of the invention include sodium oleyl succinate, ammonium lauryl sulphosuccinate, sodium lauryl ether sulphosuccinate, sodium dodecylbenzene sulphonate, triethanolamine dodecylbenzene sulphonate, lauryl ether carboxylic acid and sodium N-lauryl sarcosinate.

Suitable preferred additional anionic cleansing surfactants are sodium lauryl ether sulphosuccinate(n)EO, (where n is from 1 to 3), lauryl ether carboxylic acid (n) EO (where n is from 10 to 20).

Mixtures of any of the foregoing anionic cleansing surfactants may also be suitable.

If added, the total amount of additional anionic cleansing surfactant in shampoo compositions of the invention may generally range from 0.5 to 45 wt. %, preferably from 1.5 to 35 wt. %, more preferably from 5 to 20 wt. %, calculated by total weight anionic cleansing surfactant based on the total weight of the composition.

When conditioning benefits are to be delivered through the hair care composition of the invention the composition comprises a conditioning agent. Typically, the most popular conditioning agents used in hair care compositions are water-insoluble oily materials such as mineral oils, naturally occurring oils such as triglycerides and silicone polymers. Conditioning benefit is achieved by the oily material being deposited onto the hair resulting in the formation of a film, which makes the hair easier to comb when wet and more manageable when dry. An especially useful conditioning agent is a silicone compound, preferably a non-volatile silicone compound. Advantageously compositions herein may include one or more silicones. The silicones are conditioning agents found in dispersed or suspended particulate form. They are intended to deposit onto hair remaining behind after rinsing of the hair with water. Suitable silicone oils may include polyalkyl siloxanes, polyaryl siloxanes, polyalkylaryl siloxanes, polyether siloxane copolymers and mixtures thereof. Amino silicones are often formulated with shampoo compositions. Amino silicones are silicones containing at least one primary amine, secondary amine, tertiary amine or a quaternary ammonium group. High molecular weight silicone gums can also be utilized. Another useful type are the crosslinked silicone elastomers such as Dimethicone/Vinyl/Dimethicone Crosspolymers (e.g. Dow Corning 9040 and 9041).

Amounts of the silicone in compositions where present may range from about 0.01 to about 10 wt. %, preferably from about 0.1 to about 8 wt. %, more preferably from about 0.3 to about 5 wt. % by weight of the hair care compositions.

Suspending Agent

Preferably the composition of the invention further comprises a suspending agent. Suitable suspending agents are selected from polyacrylic acids, cross-linked polymers of acrylic acid, copolymers of acrylic acid with a hydrophobic monomer, copolymers of carboxylic add-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polyacrylic acid is available commercially as Carbopol 420, Carbopol 488 or Carbopol 493. Polymers of acrylic acid cross-linked with a polyfunctional agent may also be used; they are available commercially as Carbopol 910, Carbopol 934, Carbopol 941 and Carbopol 980. An example of a suitable copolymer of a carboxylic acid containing monomer and acrylic acid esters is Carbopol 1342. All Carbopol (trademark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Mixtures of any of the above suspending agents may be used. Preferred is a mixture of cross-linked polymer of acrylic acid and crystalline long chain acyl derivative.

Suspending agent, if included, will generally be present in a shampoo composition of the invention at levels of from 0.1 to 10%, preferably from 0.5 to 6%, more preferably from 0.5 to 4% by total weight of suspending agent based on the total weight of the composition.

A composition of the invention may contain other ingredients for enhancing performance and/or consumer acceptability. Such ingredients include fragrance, dyes and pigments, pH adjusting agents, pearlescers or opacifiers, viscosity modifiers, preservatives, and natural hair nutrients such as botanicals, fruit extracts, sugar derivatives and amino acids.

According to another aspect of the invention there is provided a method of maximizing the deposition of a zinc-based antidandruff agent on to scalp with a uniform deposition profile comprising the steps of applying a composition of the invention on to the desired scalp surface followed by rinsing the surface with water.

The invention will now be illustrated with reference to the following non-limiting Examples.

EXAMPLES

Example 1-6: Effect of Combination of Various ZPTO Particle Sizes and Cationic Guar as Per the Invention on the Deposition Efficiency The following shampoo compositions was prepared.

TABLE 1

| Ingredient | Wt % as active |
| --- | --- |
| Sodium Laureth Sulfate | 14.0 |
| Coco amidopropyl betaine | 1.6 |
| Guar hydroxypropyltrimonium chloride[1] | 0.2 |
| DC7128: Dimethicone | 0.8 |
| DC1788: Dimethiconol | 1.2 |
| Zinc pyrithione (as in Table -2) | 1.0 |
| Zinc heptasulphate | 0.1 |
| Sodium salicylate | 0.3 |
| Sodium hydroxide | 0.33 |
| Carbopol 980 | 0.6 |
| phenoxyethanol | 0.5 |
| Sodium chloride | 0.6 |
| Water | To 100 |

[1]The cationic guar used had a molecular weight of about 1.35 million Dalton and a degree of substitution of 0.18 sourced from Lamberti.

Table-2

The various shampoo compositions prepared above, had the ZPTO specification as given in the table-2 below. The ZPTO deposition efficiency of the various compositions were measured using an invitro model as given below.

About 0.2 grams of the shampoo composition was taken on artificial skin (VITRO-SKIN from IMS testing group). This was diluted with 1.8 ml water and rubbed with a plastic rod for 30 seconds. The surface was then rinsed two times with water, first time with 4 ml water for 30 seconds and then again with 4 ml water for 30 seconds. The ZPTO deposited on the skin was then measured using HPLC method. The average deposition (of five such experiments) and standard deviation is given in the table-2 below.

TABLE 2

| Example Number | ZPTO type | ZPTO average particle size in micrometers | ZPTO deposition, μg/plate | Std. dev |
|---|---|---|---|---|
| 1 | Amorphous | 0.21 | 3.25 | 0.27 |
| 2 | Amorphous | 0.64 | 3.64 | 0.47 |
| 3 | Amorphous | 0.43 | 4.11 | 1.33 |
| 4 | Amorphous | 2.08 | 4.80 | 1.13 |
| 5 | Amorphous | 3.04 | 5.50 | 0.74 |
| 6 | Amorphous | 4.93 | 6.08 | 1.26 |
| 7 | Platelet | 4.33 | 4.08 | 0.97 |
| 8 | Platelet | 7.33 | 4.42 | 1.04 |

The data in Table-2 above indicates that compositions as per the invention (Examples 2 to 8) provide for better ZPTO deposition as compared to an example outside the invention (Example-1).

Examples 9-11, 4-6: Effect of Particle Size on the Antimicrobial Efficacy

Shampoo samples as per Table-1 were prepared except that ZPTO samples (all of amorphous morphology) were used as shown in Table-3 below. Some of the samples (Examples 4-6) used in this test were the same as in Table-2 above.

The shampoo samples were tested for antimicrobial reduction in an anti-*malassezia* assay. The procedure used was as below.

Anti-*Malassezia* Assay

*M. furfur* was initially inoculated in Pityrosporum Broth and then transferred into agar slurry, to bring it to a final concentration of approximately 2 to $6 \times 10^6$ cells/ml. Vitro-Skin™ was sandwiched in a plastic ring support, with its rough topography facing up. After treating with 0.2 g of shampoo and rinsing off twice with 1.8 ml water, the Vitro-Skin™ ring was placed onto a Modified Dixon Agar plate and 0.2 ml sodium chloride solution with *M. furfur* which was gently pipetted onto the rough skin surface. Following incubation for 24 hours, the Vitro-Skin™ was placed in a vial containing 10 ml Butterfield's phosphate buffer and then vortexed and ultrasonically treated. 20•l of $10^0$ to $10^{-3}$ dilutions of the above solution was plated onto Modified Dixon Agar plates, and incubated for another 3 to 4 days. The number of colonies on each plate was then counted, and the final numbers were determined by multiplying by the appropriate dilution. The log reduction of each sample was calculated as follows and averaged from three replicates.

Log reduction=$Log_{10}CFU_{(Sample)}$–$Log_{10}CFU_{(water\ control)}$

The samples along with the data on the log kill is shown in Table-3 below.

TABLE 3

| Example Number | ZPTO average particle size in micrometers | Log reduction (cfu/ml) | Std. dev |
|---|---|---|---|
| 9 | 0.25 | −1.42 | 0.10 |
| 10 | 0.50 | −1.85 | 0.10 |
| 11 | 1.00 | −1.74 | 0.03 |
| 4 | 2.08 | −2.02 | 0.07 |
| 5 | 3.04 | −1.84 | 0.10 |
| 6 | 4.93 | −1.33 | 0.19 |

The data in Table-3 above indicates that all shampoo samples as per the invention gives good log reduction while those with ZPTO at particle size between 0.5 and 3 microns exhibit better efficacy in this respect.

Examples 12-14: Effect of Different Types of Cationic Guar in Shampoo Compositions on Uniform Distribution of ZPTO on the Scalp Shampoo compositions as shown in Table-4 below were prepared.

TABLE 4

| Ingredient | Example - 12, Wt % as active | Example - 13, Wt % as active | Example - 14, Wt % as active |
|---|---|---|---|
| Sodium Laureth Sulfate | 14.0 | 14.0 | 14.0 |
| Coco amidopropyl betaine | 1.6 | 1.6 | 1.6 |
| Guar hydroxypropyltrimonium chloride, type | A | B | C |
| Guar hydroxypropyltrimonium chloride, wt % | 0.2 | 0.2 | 0.2 |
| DC7128: Dimethicone | 0.8 | 0.8 | 0.8 |
| DC1788: Dimethiconol | 1.2 | 1.2 | 1.2 |
| Zinc pyrithione (Avergage particle size of 0.25 micrometer amorphous type) | 1.0 | 1.0 | 1.0 |
| Zinc heptasulphate | 0.1 | 0.1 | 0.1 |
| Sodium hydroxide | 0.33 | 0.33 | 0.33 |
| Carbopol 980 | 0.6 | 0.6 | 0.6 |
| Sodium chloride | 0.6 | 0.6 | 0.6 |
| Water | To 100 | To 100 | To 100 |

A: a cationic guar with a molecular weight of about 2.1 million Dalton and a degree of substitution of from 0.2 to 0.3.
B: a cationic guar with a molecular weight of about 1.35 million Dalton and a degree of substitution of 0.18.
C: a cationic guar with a molecular weight of about 1.1 million Dalton and a degree of substitution of 0.13.

The various compositions as in Table-4 were tested to measure the uniformity of deposition on the various parts of the scalp. The measurements were carried out using the following invivo protocol.

Subjects were allocated a pair of test products from the Examples 12 to 14 above according to a randomization table. They then wash using those two products, one on each half of the head (one on the right side and the other on the left side). Samples of ZPTO deposited on their scalp are then collected both in the front half and the back half of their scalp. The samples are then quantified by HPLC-PAD. The data from 121 subjects were then collected and the data on the ZPTO deposited on the front and the back is summarized in Table-5 in terms of mean of Log ZPTO equivalent (μg/cm$^2$).

TABLE 5

| Samples | Example - 12, | Example - 13 | Example - 14 |
|---|---|---|---|
| Front | −1.14 | −1.21 | 0.56 |
| Back | −3.02 | −1.92 | −1.12 |

The data in Table-5 above indicates that composition as per the invention (Example 13) provides a more uniform distribution of ZPTO as compared to compositions outside the invention (Examples 12 and 14).

The invention claimed is:
1. A hair care composition consisting of
  (i) 0.01 to 3.0% by weight of a zinc-based antidandruff agent having an average particle size of 2.08 to 8 micrometer; and

(ii) 0.04 to 2.0% by weight of a cationic modified guar deposition polymer having a molecular weight of from 1.0 million to 1.5 million Dalton and a cationic degree of substitution of from 0.16 to 0.20, wherein the cationic degree of substitution is measured using $^1$H NMR and the spectrum is recorded at 25° C.;

(iii) 0.1 to 3% of a zinc compound by weight of the composition;

(iv) 0.01 to 0.75% by weight of climbazole;

(v) 0.1 to 10% by weight of a suspending agent; and (vi) optionally one or more of a vitamin B3 compound, an anionic cleansing surfactant, a betaine surfactant, a water-insoluble oily conditioning agent, fragrance, dyes and pigments, pH adjusting agents, pearlescers or opacifiers, preservatives, or natural hair nutrients.

2. The composition as claimed in claim 1 comprising 0.01 to 1.5% zinc based antidandruff agent.

3. The composition as claimed in claim 1 wherein the zinc-based antidandruff agent is zinc pyrithione.

4. The composition as claimed in claim 1 comprising 0.04 to 0.5% of cationic modified guar deposition polymer.

5. The composition as claimed in claim 1 wherein the polymer is guar hydroxypropyl trimonium chloride.

6. The composition as claimed in claim 1, wherein said zinc compound is selected from zinc oxide, zinc citrate, zinc malonate or zinc carbonate.

7. The composition as claimed in claim 1 comprising the vitamin B3 compound.

8. The composition as claimed in claim 1 wherein the composition is a shampoo.

9. The composition as claimed in claim 1, wherein the suspending agent is selected from the group consisting of polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums, and crystalline long chain acyl derivatives.

10. The composition as claimed in claim 1 comprising an anionic cleansing surfactant.

11. A method of maximizing the deposition of a zinc-based antidandruff agent on to scalp with a uniform deposition profile comprising the steps of applying a composition as claimed in claim 1 on to the desired scalp surface followed by rinsing the surface with water.

\* \* \* \* \*